United States Patent [19]

Pelletier

[11] 4,136,125

[45] Jan. 23, 1979

[54] PREPARATION OF BIS(PENTACHLOROCYCLOPENTADIE-NYL)

[75] Inventor: Dennis C. Pelletier, Fall River, Mass.

[73] Assignee: Hooker Chemicals & Plastics Corp., Niagara Falls, N.Y.

[21] Appl. No.: 863,028

[22] Filed: Dec. 21, 1977

[51] Int. Cl.$^2$ .............................................. C07C 17/00
[52] U.S. Cl. ................................................ 260/648 R
[58] Field of Search ..................................... 260/648 R

[56] References Cited

FOREIGN PATENT DOCUMENTS 197546   7/1967   U.S.S.R. ............................ 260/648 R

*Primary Examiner*—Delbert E. Gantz
*Assistant Examiner*—Joseph A. Boska
*Attorney, Agent, or Firm*—Peter F. Casella; William J. Crossetta, Jr.; Arthur S. Cookfair

[57] ABSTRACT

Bis(pentachlorocyclopentadienyl) is prepared by reductive coupling of hexachlorocyclopentadiene with cuprous chloride in an alcoholic reaction medium. The product is extracted with the aid of an organic solvent, such as orthochlorotoluene. The organic solvent containing the dissolved product together with unreacted cuprous chloride is then treated with hydrochloric acid, having a strength of at least 0.4 normal, to extract the cuprous chloride, and then with water to dissolve residual acid. The solvent is then further processed, for example, by crystallization, to recover $C_{10}Cl_{10}$ product.

10 Claims, No Drawings

PREPARATION OF BIS(PENTACHLOROCYCLOPENTADIENYL)

BACKGROUND OF THE INVENTION

This invention comprises an improved process for the preparation of bis(pentachlorocyclopentadienyl), a known chlorocarbon characterized by the empirical formula $C_{10}Cl_{10}$, known to be useful as an insecticide and as a vulcanizing agent as well as an intermediate in preparation of other useful chlorinated organic chemicals.

Various methods for the preparation of bis(pentachlorocyclopentadienyl) have been described in the chemical literature and have been employed in laboratory or commercial scale preparations. Typically, such methods involve the reductive coupling of hexachlorocyclopentadiene with the aid of a reducing agent such as hydrogen, metallic copper, or cuprous chloride. Generally the preparation is effected in the liquid phase utilizing an organic liquid reaction medium, that is a solvent for the reactants and/or the product.

Cuprous chloride has been found to be a particularly effective agent for the reductive coupling of hexachlorocyclopentadiene. U.S. Pat. No. 2,849,499 discloses a process for the preparation of bis(pentachlorocyclopentadienyl) by reaction of cuprous chloride and hexachlorocyclopentadiene in an aqueous ethanol reaction medium. The impure $C_{10}Cl_{10}$ product is formed as a sludge which is subsequently separated by decantation of the liquid and then washed first with hydrochloric acid, then twice with ethanol. The sludge is then dissolved in petroleum ether, decolorized twice with activated charcoal and crystallized from solution. Although the process provides a useful method for the preparation of $C_{10}Cl_{10}$, difficulties are encountered when it is carried out on a commercial scale. In particular, it has been found that the sludge, which comprises the crude $C_{10}Cl_{10}$ product, must be subjected to multiple purification steps, especially washings which require filtration. The sludge, however, is formed of extremely small particles which tend to pack closely and are filtered with considerable difficulty. It has been found that such difficulties may be avoided by extracting the $C_{10}Cl_{10}$ product from an alcoholic reaction medium with the aid of a suitable organic solvent, such as toluene, then treating the organic solvent with a weak aqueous hydrochoric acid solution, such as about 0.25 N, to remove unreacted cuprous chloride and subsequently recovering the $C_{10}Cl_{10}$ product by crystallization from the organic solvent. The hydrochloric acid treatment provides an effective means of purification of the final product by the extraction of unreacted cuprous chloride. Residual HCl may be removed from the organic solvent by extraction with water prior to crystallization of $C_{10}Cl_{10}$ product. It has been found, however, that the organic solvent phase, containing the dissolved product, is a highly corrosive liquid, typically having a pH in the range of about 3.0–3.5, even after removal of the hydrochloric acid and water washing of the organic solvent phase. The highly corrosive nature of this organic liquor presents problems in further processing, for example, in transferring through pipes, treatment in a crystallizing vessel, and centrifuging to remove the product after crystallization, due to its corrosive action on typical materials of processing equipment. Attempts to increase the pH of the organic solvent liquor and thereby reduce its corrosive activity, through the use of a weaker hydrochloric acid extraction medium, have proven unsuccessful. However, it has been found, surprisingly, that the pH of the organic solvent liquor may be substantially increased, for example to about 6.0 to about 7.0, and its corrosive characteristics decreased accordingly, when a stronger acid, such as about 4.0 N or greater is employed in the hydrochloric acid treatment step.

It will be appreciated that although bis(pentachlorocyclopentadienyl) may be effectively prepared in a known manner, such as by reductive coupling of hexachlorocyclopentadiene with the aid of a reducing agent such as cuprous chloride in an alcoholic medium, a need exists for improved methods for the recovery and purification of the product.

It is an object of this invention to provide an improved process for the preparation of bis(pentachlorocyclopentadienyl). It is a further object to provide an improved method for the extraction and purification of bis(pentachlorocyclopentadienyl) product from an alcohol reaction medium.

SUMMARY OF THE INVENTION

In accordance with this invention there is provided a process for the preparation of bis(pentachlorocyclopentadienyl) which comprises the steps of
 (a) reductively coupling hexachlorocyclopentadiene by reaction with cuprous chloride in an alcohol reaction medium;
 (b) extracting the bis(pentachlorocyclopentadienyl) product from the reactin medium by addition thereto of an organic solvent that is immiscible with the alcohol, and allowing the alcohol and organic solvent to settle, forming two phases;
 (c) separating the alcohol phase;
 (d) treating the organic solvent to extract unreacted cuprous chloride therefrom by addition of hydrochloric acid having a strength of at least about 0.4 normal, and allowing the organic solvent and hydrochloric acid to separate into two phases; and
 (e) recovering the bis(pentachlorocyclopentadienyl) product from the organic solvent phase.

The first step in the preparation of $C_{10}Cl_{10}$, that is the reaction between hexachlorocyclopentadiene and cuprous chloride, is preferably carried out in the presence of a suitable inert liquid diluent that serves as a solvent for the by-product cupric chloride formed in the reaction and which is a substantial non-solvent for the $C_{10}Cl_{10}$ formed. Preferred liquid diluents for this purpose include the lower alkanols preferably 1–4 carbon atoms, and mixtures thereof with water. Most preferred are aqueous mixtures of methanol or ethanol, especially aqueous methanol solutions containing about 5 to about 45% and most preferably about 15 to about 25% water. It is preferred to employ a slight stoichiometric excess of the hexachlorocyclopentadiene reactant. The reaction may be carried out over a wide range of temperatures for example between about 0° and about 100° Celsius, the practical upper limit being the boiling point of the alcohol or aqueous alcohol reaction medium. The reaction is preferably carried out at atmospheric pressure although superatmospheric pressure may be employed. It is preferred to maintain a reaction temperature of about 15 to about 40° Celsius, and most preferably about 20 to about 35° Celsius. The reaction, which is slightly exothermic, may require cooling to maintain the reaction temperature in the most preferred range. Following the reaction, an organic solvent is added and mixed with the reaction medium to extract the solid $C_{10}Cl_{10}$ formed. The solvent is added and mixed with the alcohol reaction medium in proportions sufficient to dissolve all, or any desired amount, of the $C_{10}Cl_{10}$ product. Preferably the resultant mixture is heated to a temperature of about 40° to 80° Celsius and most preferably about 50° to 60° Celsius. Thus, the amount of organic solvent added may vary considerably but will typically be in the range of about 0.20 to about 1.0 parts by weight of solvent per part of hexachlorocyclopentadiene reactant. Suitable organic solvents are those which are solvents for the $C_{10}Cl_{10}$ product and which are substantially immiscible with the alcohol water phase, including, for example, xylene, toluene, orthochlorotoluene, and parachlorotoluene. The preferred solvent, based on lower volatility and higher flash point, is monochlorotoluene, most preferably orthochlorotoluene. In addition, it has been found that improved phase separations are achievable when orthochlorotoluene is employed.

Following treatment with the organic solvent the reaction medium is allowed to settle, typically resulting in a phase separation wherein the alcohol or alcohol-water containing dissolved cupric chloride forms an upper phase and the organic solvent containing dissolved $C_{10}Cl_{10}$ product as well as unreacted cuprous chloride and hexachlorocyclopentadiene forms a lower phase. The upper phase is removed, for example, by decantation. The lower phase is then treated with aqueous hydrochloric acid preferably at a temperature of about 50° to about 80° Celsius to extract the cuprous chloride therefrom and allowed to settle, again forming two phases: an upper phase of aqueous HCl, containing copper salts, and a lower phase of organic solvent, containing the $C_{10}Cl_{10}$ product and unreacted hexachlorocyclopentadiene. The upper phase is removed, for example, by decantation. The hydrochloric acid is preferably in an amount of about 1 to about 3 parts by weight of acid per part by weight of cuprous chloride reactant employed initially. It is an important aspect of this invention that the hydrochloric acid treatment of the organic solvent be carried out using hydrochloric acid of at least about 0.4 normality. When hydrochloric acid of a strength substantially below that such as about 0.25 normal is employed the remaining organic solvent liquor is highly corrosive in nature, typically characterized by a pH in the range of about 4. The corrosive nature of this liquor presents substantial problems in further processing, particularly with respect to its corrosive action on typical materials of processing equipment. Attempts to increase the pH of the solvent mixture and thereby reduce its corrosive activity, through the use of a weaker hydrochloric acid extraction medium have proven unsuccessful. However, it has been found, surprisingly, that when a hydrochloric acid extraction medium of substantially higher acidity, such as in the range of about 0.4 N to about 1.0 N is employed, the organic solvent phase, following the HCl extraction, is substantially lower in acidity and is generally characterized by a pH in the range of about 6.0 to about 7.0. For this reason, the HCl extraction step in the process of this invention, is carried out, using a hydrochloric acid of at least about 0.4 normality and preferably about 0.4 to about 0.6 normality.

Following removal of the upper phase (acid) the organic solvent containing the dissolved product may be further treated with water to remove any residual hydrochloric acid values and purged with nitrogen gas, if desired. Preferably, water is added and mixed with the organic solvent in amounts by weight of about 0.1 to about 3 parts of water per art of organic solvent present, although lesser or greater proportions of water may be employed if desired. After mixing for a period of time such as from a few minutes to about an hour or more, preferably at a temperature of about 50° to about 80° Celsius, the liquid mixture is allowed to settle, forming an upper water phase and a lower organic solvent phase. The water phase may be conveniently separated, for example, by decantation.

The organic solvent may then be cooled slowly, for example from an initial temperature in the range of about 50° to about 100° Celsius to a final temperature of below about 30° Celsius, to cause the $C_{10}Cl_{10}$ product to crystallize from solution. The crystalline product may then be collected, for example by filtration.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

A mixture of 936 parts of hexachlorocyclopentadiene, 1166 parts of methanol and 276 parts of water was heated to about 25° to 30° C. and maintained at that temperature while 324 parts of CuCl was added. The CuCl was added in granular form, slowly, with agitation, over a period of about two hours to avoid excessive exotherm. Following the addition of the CuCl, the reaction mixture was held at a temperature of about 25° to 30° C. with agitation, for an additional four hours to allow the reaction to proceed toward completion. Then 427 parts of toluene was added to the reaction mixture and the mixture heated to about 55° C. and maintained thereat, with stirring, for about one hour. The mixture was then allowed to settle, without agitation, for about one half hour with a resultant formation of two liquid phases — an upper phase comprising, methanol, water and cupric chloride, and a lower phase containing toluene and dissolved $C_{10}Cl_{10}$ product as well as unreacted hexachlorocyclopentadiene and cuprous chloride. The upper phase was removed by decantation. The remaining organic phase was treated by addition of 631 parts 0.25 N hydrochloric acid. The mixture was heated to about 75° C. and maintained thereat for about one hour, with agitation, then allowed to settle for about ½ hour. Upon settling, the mixture separated into two phases — an upper aqueous acid phase containing copper salts, and a lower organic phase containing toluene and dissolved $C_{10}Cl_{10}$ product as well as unreacted hexachlorocyclopentadiene. The upper phase was removed by decantation. The remaining organic phase was further treated by addition of 613 parts of water. The resultant mixture was heated to about 75° C. and maintained thereat for about one hour, with agitation, then allowed to settle for about ½ hour, whereupon the water separated, forming an upper phase. The water phase was removed by decantation. Acidity measurements of the organic phase indicated a pH of 3.0. The organic phase was then cooled slowly, over a period of about 8½ hours, with slow agitation, from about 75° C. to about 5° C., to crystallize the $C_{10}Cl_{10}$ product from solution.

The resultant slurry was filtered and the filter cake was washed over with toluene and and three times with methanol then vacuum dried to yield 354 parts of bis(pentachlorocyclopentadienyl) product.

EXAMPLE 2

The procedure of Example 1 was repeated except that in the hydrochloric acid treatment of the organic phase, the 631 parts of 0.25N HCl was replaced by 616 parts of 0.5N HCl. Following the HCl treatment and separation of the aqueous acid phase, the acidity of the organic phase was measured and found to be a pH of 6.4. The dissolved product was crystallized from the toluene solvent and the crystals were collected by filtration and washed with toluene and methanol as in Example 1, to yield a total of 449.2 parts of bis(pentachlorocyclopentadienyl) product.

EXAMPLE 3

The procedure of Example 2 was repeated except that in place of the 427 parts of toluene solvent, there was substituted 502 parts of orthochlorotoluene. After treatment of the organic phase with 0.5N HCl, and removal of the aqueous acid phase, the pH of the organic phase was measured and found to be 7.0. The crystalline product was separated from the organic phase by centrifugation, then washed with toluene and methanol and dried to yield 363 parts of large, bright yellow crystals of bis (pentachlorocyclopentadienyl) product. It was found that the substitution of orthochlorotoluene in place of toluene resulted in a substantially sharper phase separation between the orthochlorotoluene and the aqueous alcohol phase as well as between the orthochlorotoluene and the alcohol-water phase.

EXAMPLE 4

The procedure of Example 3 was repeated except that the acid and water treatment of the organic phase was varied as follows: The organic phase was first treated with 359 parts of 1.9N HCl, then with 291 parts of water. Following the acid treatment, the pH of the organic phase was found to be 6.7. Upon separation and washing of the crystalline product there was obtained 451.4 parts of bis(pentachlorocyclopentadienyl).

EXAMPLE 5

The process of Example 2 was repeated except that the acid and water treatment of the organic phase was varied as follows: The organic phase was first treated with 358 parts of 1.9N HCl, then with 582 parts of water. Following the acid treatment, the pH of the organic phase was measured and found to be 6.7. Upon separation and washing of the crystalline product, there was obtained 383.4 parts of bis(pentachlorocyclopentadienyl).

What is claimed is:

1. A process for the preparation of bis(pentachlorocyclopentadienyl) which comprises the steps of
   (a) reductively coupling hexachlorocyclopentadiene by reaction with cuprous chloride in an alcohol reaction medium;
   (b) extracting the bis(pentachlorocyclopentadienyl) product from the reaction medium by addition thereto of an organic solvent that is immiscible with the alcohol, and allowing the alcohol and organic solvent to settle, forming two phases;
   (c) separating the alcohol phase;
   (d) treating the organic solvent to extract unreacted cuprous chloride therefrom by addition of hydrochloric acid having a strength of at least about 0.4 normal, and allowing the organic solvent and hydrochloric acid to separate, forming two phases; and
   (e) recovering the bis(pentachlorocyclopentadienyl) product from the organic solvent phase.

2. A process according to claim 1 wherein the alcohol reaction medium is a methanol-water mixture having a water content of about 5 to about 45 percent by weight of water.

3. A process according to claim 2 wherein step (a) is carried out at about 15° to about 40° Celsius.

4. A process according to claim 3 wherein the organic solvent is selected from the group consisting of toluene, xylene, orthochlorotoluene, parachlorotoluene and mixtures thereof.

5. A process according to claim 4 wherein step (d) comprises adding hydrochloric acid of a normality of about 0.4 to about 1.0, to the reaction mixture in an amount of about 1 to about 3 parts by weight of acid per part of cuprous chloride reactant, heating the resultant mixture, with agitation, to about 50° to about 80° Celsius, and then allowing the mixture to settle without agitation, to form an upper hydrochloric acid phase and a lower organic solvent phase.

6. A process according to claim 5 wherein the organic solvent phase is cooled from an initial temperature in the range of about 50° to about 80° Celsius to a final temperature of below about 20° Celsius with the resultant precipitation of crystals of bis(pentachlorocyclopentadienyl) from solution and the crystals are separated and recovered from the organic solvent.

7. A process according to claim 6 wherein the organic solvent phase is additionally treated by mixing with water in an amount of about 0.1 to about 3 parts of water per part of organic solvent at a temperature of about 50° to about 80° Celsius, following the removal of the hydrochloric acid phase.

8. A process according to claim 6 wherein the hydrochloric acid is of a normality of about 0.4 N to about 0.6 N.

9. A process according to claim 8 wherein the organic solvent is orthochlorotoluene.

10. A process for the preparation of bis(pentachlorocyclopentadienyl) which comprises the steps of:
    (a) reductively coupling hexachlorocyclopentadiene by reaction with cuprous chloride in a liquid reaction medium comprising a methanol-water mixture having a water content of about 15 to about 25 percent of water at a temperature of about 20° to about 35° Celsius;
    (b) extracting the bis(pentachlorocyclopentadienyl) product from the reaction medium by addition thereto of orthochlorotoluene in an amount of about 0.2 to about 1.0 part by weight of orthochlorotoluene per part of hexachlorocyclopentadiene reactant, and heating the resultant mixture to a temperature of about 50° to about 60° Celsius, and subsequently allowing the mixture to settle, forming an orthochlorotoluene phase and a methanol-water phase;
    (c) separating the methanol-water phase;
    (d) treating the orthochlorotoluene phase to extract cuprous chloride therefrom, by adding and mixing therewith hydrochloric acid of about 0.4 N to about 0.5 N in an amount of about 1 to about 3 parts of hydrochloric acid per part of initial cuprous chloride reactant, at a temperature of about 50° to about 80° Celsius, and subsequently allowing the mixture to settle, forming an orthochlorotoluene phase and a hydrochloric acid phase;
(e) separating the hydrochloric acid phase;
(f) crystallizing the bis(pentachlorocyclopentadienyl) from solution by cooling the orthochlorotoluene phase from an initial temperature in the range of about 50° to about 80° Celsius to a final temperature of below about 20° Celsius; and
(g) separating the bis(pentachlorocyclopentadienyl) crystals from the orthochlorotoluene.

* * * * *